(12) United States Patent
Bitton

(10) Patent No.: US 11,705,222 B1
(45) Date of Patent: Jul. 18, 2023

(54) METHOD OF REDUCING GREENHOUSE GAS EMISSIONS FROM RECYCLING ALUMINUM ALLOY WHEELS

(71) Applicant: House of Metals Company Limited, Toronto (CA)

(72) Inventor: Daniel Bitton, Toronto (CA)

(73) Assignee: House of Metals Company Limited, Toronto (CA)

(*) Notice: Subject to any disclaimer, the term of this patent is extended or adjusted under 35 U.S.C. 154(b) by 0 days.

(21) Appl. No.: 18/101,177

(22) Filed: Jan. 25, 2023

Related U.S. Application Data

(60) Provisional application No. 63/329,663, filed on Apr. 11, 2022.

(51) Int. Cl.
- *B24C 1/10* (2006.01)
- *G16C 20/10* (2019.01)
- *G06Q 10/30* (2023.01)
- *G06Q 30/018* (2023.01)

(52) U.S. Cl.
CPC ............ *G16C 20/10* (2019.02); *B24C 1/10* (2013.01); *G06Q 10/30* (2013.01); *G06Q 30/018* (2013.01)

(58) Field of Classification Search
CPC .......... G16C 20/10; B24C 1/10; G06Q 10/30; G06Q 30/018
See application file for complete search history.

(56) References Cited

U.S. PATENT DOCUMENTS

| | | | | |
|---|---|---|---|---|
| 6,099,659 A * | 8/2000 | Tacito | ............... | G01N 33/442 209/11 |
| 6,983,901 B2 * | 1/2006 | Bitton | ............... | C22B 21/0069 241/24.15 |
| 9,475,652 B2 * | 10/2016 | Nichols | ............... | B07C 5/3422 |
| 10,220,418 B2 | 3/2019 | Bitton | | |
| 11,263,599 B2 * | 3/2022 | Guyer | ............... | B09B 3/25 |
| 2014/0365002 A1 | 12/2014 | Nichols et al. | | |
| 2017/0173636 A1 | 6/2017 | Bitton | | |

FOREIGN PATENT DOCUMENTS

| | | |
|---|---|---|
| WO | 2019099453 A1 | 5/2019 |

OTHER PUBLICATIONS

International Search Report and Written Opinion in respect of International Application No. PCT/CA2023/050086 dated Mar. 29, 2023.

* cited by examiner

*Primary Examiner* — Ryan J. Walters
(74) *Attorney, Agent, or Firm* — Bereskin & Parr LLP/S.E.N.C.R.L., s.r.l.

(57) ABSTRACT

A method of recycling aluminum alloy wheels, the method may comprise (a) providing a feed of aluminum alloy wheels; (b) fragmenting the aluminum alloy wheels into a plurality of fragments; (c) shot blasting the plurality of fragments to at least partly remove at least one contaminant material; (d) storing at least one recognition criterion and at least one carbon factor; (e) for each fragment of a representative sample of fragments, determining, for each contaminant material, a contaminant material concentration estimate for that fragment; (f) operating a data processor to either approve or reject the plurality of fragments, based on an aggregate carbon emission calculation being based on the contaminant material concentration estimate and the carbon factor. When the plurality of fragments is approved, they may be provided to a downstream recycling process. When the plurality of fragments is rejected, they may be further shot blasted.

18 Claims, 1 Drawing Sheet

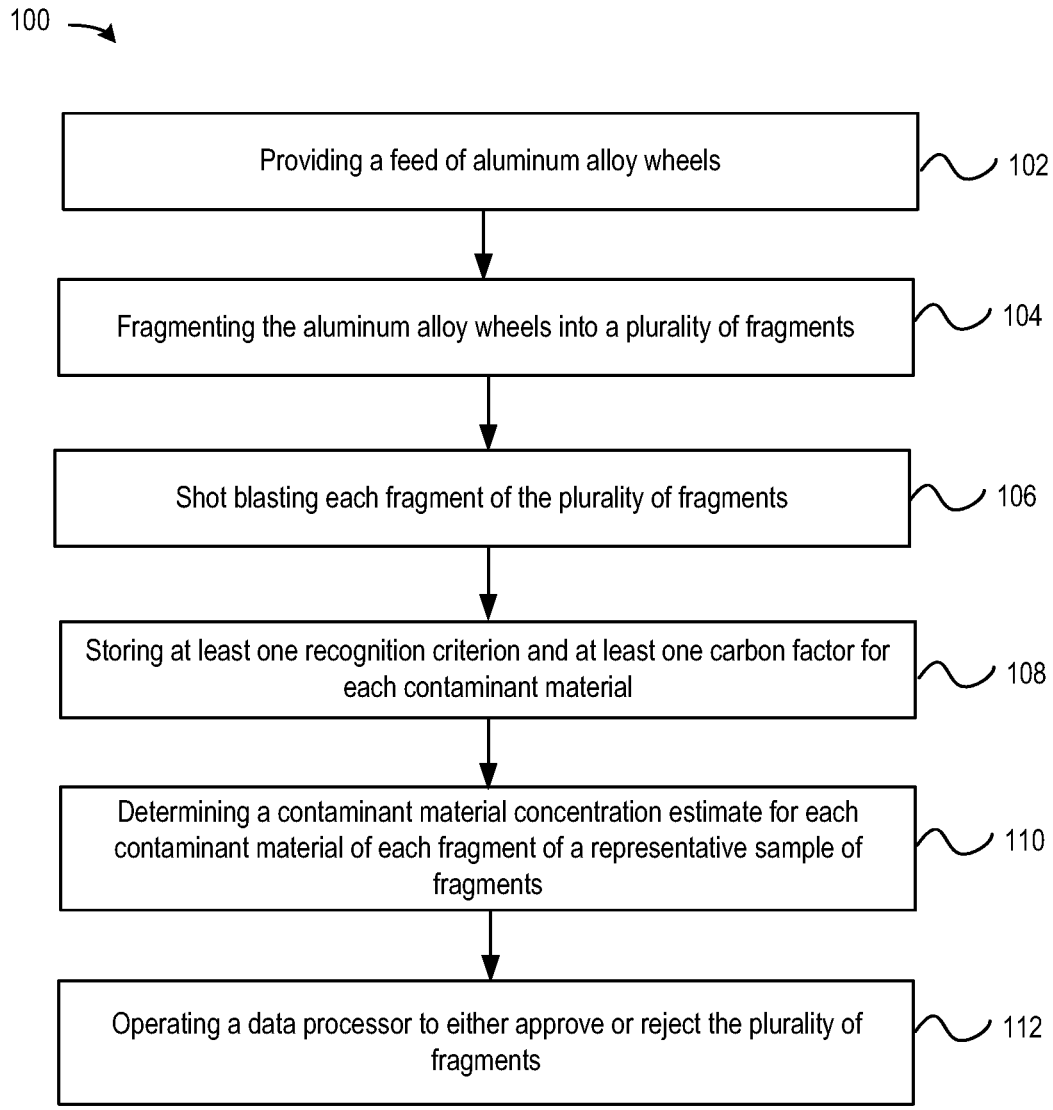

METHOD OF REDUCING GREENHOUSE GAS EMISSIONS FROM RECYCLING ALUMINUM ALLOY WHEELS

RELATED APPLICATION

This application claims the benefit of U.S. Provisional Patent Application No. 63/329,663, filed Apr. 11, 2022, which is incorporated herein by reference in its entirety.

FIELD

The described embodiments relate to the field of recycling, and in particular, to the use of an aggregate carbon emission calculation for reducing greenhouse gas emissions during the recycling process.

BACKGROUND

Recycling what would otherwise be waste materials to form new materials or objects is important in modern waste management. Many different materials can be recycled, for example, glass, paper, cardboard, metal, plastic, tires, textiles, batteries, and electronics. The typical method for recycling waste material includes pickup, sorting, cleaning, and processing.

Metals are of particular value for recycling. Unlike other materials, metals may be recycled into products of substantially similar quality to their feed material.

Metals provided for recycling however can sometimes be contaminated by surface contaminants that can affect their recyclability in addition to their elemental composition when melted during the recycling process.

SUMMARY

This summary is intended to introduce the reader to various aspects of the applicant's teaching, but not to define any specific embodiments. In general, disclosed herein are one or more methods of recycling waste metal.

In a first aspect, some embodiments of the invention provide a method of recycling aluminum alloy wheels, the method may comprise:
  providing a feed of aluminum alloy wheels of a particular alloy;
  fragmenting the aluminum alloy wheels into a plurality of fragments;
  shot blasting the plurality of fragments to at least partly remove at least one contaminant material, each contaminant material of the at least one contaminant material i) comprising at least one of paint, plastic or rubber, ii) containing carbon, and iii) being combustible;
  storing in a computer readable non-transient memory, at least one recognition criterion and at least one carbon factor, wherein
    for each contaminant material of the at least one contaminant material, the at least one recognition criterion comprises a recognition criterion for that contaminant material, and
    for each contaminant material of the at least one contaminant material, the at least one carbon factor comprises a carbon factor for that contaminant material, the carbon factor indicating a proportion of carbon in that contaminant material such that combustion of a quantity of that contaminant material would produce a corresponding quantity of carbon emissions calculable using the carbon factor;
  for each fragment of a representative sample of fragments of the plurality of fragments,
    for each contaminant material of the at least one contaminant material, using the recognition criterion for that contaminant material to determine a contaminant material concentration estimate for that fragment;
  operating a data processor to either approve or reject the plurality of fragments, based on an aggregate carbon emission calculation for the plurality of fragments, the aggregate carbon emission calculation being based on, for each contaminant material of the at least one contaminant material, and for each fragment of the representative sample of fragments, the contaminant material concentration estimate and the carbon factor for that contaminant material;
  when the plurality of fragments is approved, providing the plurality of fragments to a downstream recycling process to produce a target aluminum alloy; and
  when the plurality of fragments is rejected, further shot blasting the plurality of fragments to further remove the at least one contaminant material.

According to some aspects of some embodiments of the present invention, the at least one contaminant material may be at least two contaminant materials, comprising at least a first contaminant material and a second contaminant material;
  for each fragment of the representative sample of fragments, determining, for each contaminant material of the at least two contaminant materials, the contaminant material concentration estimate for that fragment, may comprise determining a first contaminant material concentration estimate for the first contaminant material in that fragment and a second contaminant material concentration estimate for the second contaminant material in that fragment; and,
  operating the data processor to either approve or reject the plurality of fragments based on the aggregate carbon emission calculation for the plurality of fragments, may comprise
    determining a first contaminant material carbon contribution based on the first contaminant material concentration estimate and the carbon factor for the first contaminant material,
    determining a second contaminant material carbon contribution based on the second contaminant material concentration estimate and the carbon factor for the second contaminant material, and
    making the aggregate carbon emission calculation based at least partly on a sum of the first contaminant material carbon contribution and the second contaminant material carbon contribution.

According to some aspects of some embodiments of the present invention, the carbon factor for the first contaminant material may differ from the carbon factor for the second contaminant material According to some aspects of some embodiments of the present invention, the recognition criterion may comprise a contaminant ingredient concentration range for at least one contaminant ingredient of that contaminant material.

According to some aspects of some embodiments of the present invention, the recognition criterion may comprise a plurality of contaminant ingredients indicative of that contaminant material.

According to some aspects of some embodiments of the present invention, a contaminant ingredient of the at least one contaminant ingredient may be different from carbon.

According to some aspects of some embodiments of the present invention, a contaminant ingredient of the at least one contaminant ingredient may not contain carbon.

According to some aspects of some embodiments of the present invention, the at least one contaminant material may comprise a metal-containing material, the at least one contaminant ingredient for that metal-containing material may comprise a kind of metal; and the recognition criterion for that metal-containing material may comprise the contaminant ingredient concentration range for that kind of metal in the metal-containing material.

According to some aspects of some embodiments of the present invention, the kind of metal may be zinc or titanium.

According to some aspects of some embodiments of the present invention, the metal-containing material may comprise paint.

According to some aspects of some embodiments of the present invention, for each fragment of the representative sample of fragments of the plurality of fragments, determining, for the metal-containing material, a contaminant material concentration estimate for that fragment may comprise heating a surface of the fragment to a point where the surface will emit a characteristic radiation while cooling down, operating a sensor to detect that characteristic radiation, and operating a processor to analyze the characteristic radiation to determine the composition measurements of the kind of metal contained within that material.

In a second aspect, some embodiments of the invention provide a method of recycling aluminum alloy wheels, the method may comprise:
   providing a feed of aluminum alloy wheels of a particular alloy;
   fragmenting the aluminum alloy wheels into a plurality of fragments;
   shot blasting the plurality of fragments to at least partly remove at least one contaminant material, each contaminant material of the at least one contaminant material i) comprising at least one of paint, plastic or rubber, ii) containing carbon, and iii) being combustible;
   after shot blasting, selecting a representative sample of fragments from the plurality of fragments;
   for each fragment of the representative sample of fragments of the plurality of fragments, for each contaminant material of the at least one contaminant material, using a recognition criterion for that contaminant material to determine a contaminant material concentration estimate for that fragment, wherein the recognition criterion for that contaminant material is stored in a computer readable non-transitory memory,
   operating a data processor to either approve or reject the plurality of fragments, based on an aggregate carbon emission calculation for the plurality of fragments, the aggregate carbon emission calculation being based on, for the at least one non-removed contaminant material of the at least one contaminant material, and for each fragment of the representative sample of fragments, the contaminant material concentration estimate and a carbon factor for that non-removed contaminant material, wherein the carbon factor for that non-removed contaminant material is stored in the computer readable non-transitory memory.

According to some aspects of some embodiments of the present invention, the method may further comprise, prior to the operating step, storing at least one of the recognition criterion and the carbon factor in the computer readable non-transient memory.

According to some aspects of some embodiments of the present invention, the method may further comprise providing the plurality of fragments to a downstream recycling process to produce a target aluminum alloy when the plurality of fragments is approved.

According to some aspects of some embodiments of the present invention, the method may further comprise providing the plurality of fragments to a shot blaster for further shot blasting when the plurality of fragments is rejected.

According to some aspects of some embodiments of the present invention, the method may further comprise discarding the plurality of fragments when the plurality of fragments is rejected.

BRIEF DESCRIPTION OF THE DRAWINGS

These and other advantages of the instant invention will be more fully and completely understood in conjunction with the following detailed description of embodiments and aspects of the present invention with reference to the following drawings, in which:

FIG. 1, in a flow chart, illustrates a method of recycling aluminum alloy wheels.

DESCRIPTION OF EXEMPLARY EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

Reference is first made to FIG. 1, in which a method 100 of recycling aluminum alloy wheels is shown. As shown in FIG. 1, the method 100 of recycling aluminum allow wheels begins at step 102, in which a feed of aluminum alloy wheels of a particular alloy is provided.

While FIG. 1 shows a method of recycling aluminum alloy wheels, and the discussion herein uses aluminum alloy wheels as an example, it is to be understood that this disclosure is not meant to be limited to methods of recycling aluminum alloy wheels. For example, the methods described herein may be applied to methods for recycling waste metal pieces, for example waste metal pieces composed of aluminum alloys (e.g., A356.2 aluminum alloys). In other examples, the waste metal pieces may be any one of bismuth alloys, brass alloys, cobalt alloys, copper alloys, gallium alloys, gold alloys, indium alloys, iron alloys, lead alloys, magnesium alloys, mercury alloys, nickel alloys, potassium alloys, silver alloys, steel alloys, tin alloys, titanium alloys, zinc alloys, zirconium alloys, etc.

As shown in FIG. 1, the provided feed of aluminum alloy wheels may be of a particular alloy. While the feed of aluminum alloy wheels may be of a particular alloy, the composition of the aluminum alloy wheels may vary. In some examples, the composition of each aluminum alloy wheel may be two different compositions present in the feed. In other examples, each aluminum wheel may be one composition of any number of different compositions present in the feed of aluminum wheels. The composition of one aluminum alloy wheel may differ from the composition of another aluminum alloy wheel because alloys of the same type can have any concentration of specific elements within a range. Further, the composition of one aluminum alloy wheel may differ from the composition of another aluminum alloy wheel due to contaminants that may be located on an external surface of at least one of the aluminum wheels.

In a typical feed of aluminum alloy wheels, at least some of the aluminum alloy wheels may be contaminated (i.e., may contain contaminant materials). Containment materials may be coatings, such as paints, plastic coatings, rubber coatings, clearcoat, chrome plating, lead weights, brass, brass fittings, stainless steel, or iron inserts. A subset of contaminant materials can include, for example, combustible materials containing carbon, such as organic materials (i.e., paints plastics, rubbers, etc.).

When melted during the recycling process, these carbon-containing contaminants may produce undesired high levels of greenhouse gases. Accordingly, these greenhouse gases may be filtered using air pollution control devices, such as baghouse filters to limit the effect these greenhouse gases have on the environment and/or to comply with regulations. To reduce costs associated with the use of air pollution control devices, it may be desirable to remove the aluminum alloy wheels and/or fragments of aluminum alloy wheels having relatively high levels of combustible carbon-containing contaminant materials from the feed prior to melting the wheels during the recycling process. That is, as discussed in more detail below, it may be desirable to have a method of recycling aluminum alloy wheels in which a plurality of fragments may be removed (i.e., discarded or redirected for further contaminant removal (i.e., cleaning)) from a recycling process to reduce the greenhouse gases produced by the recycling method. In the portion of the description that follows, "contaminants" means carbon-containing contaminants that may produce undesirably high levels of greenhouse gases, unless specifically noted otherwise.

In some cases, the composition of the aluminum alloy wheels provided at step 102 may be measured, prior to the fragmentation step 104 and the shot blasting step 106, to identify contaminant materials contained in the feed of aluminum alloy wheels. In some cases, a level of contamination of the aluminum alloy wheels may also be determined, for example, by determining the concentration of each of the identified contaminant materials in a particular aluminum alloy wheel or within the feed of aluminum wheels. The composition of the aluminum alloy wheels may be analyzed using any suitable composition analyzer known in the art, including but not limited to analyzers that use radiation emitters to induce characteristic radiation to be emitted from the aluminum alloy wheels. Other suitable composition analyzers may compare expected properties of an aluminum alloy wheel with the actual properties of the aluminum alloy wheel to identify the presence of a contaminant material and the type of contaminant.

In some cases, identifying a contaminant material may involve determining a recognition criterion for that contaminant material, that is, the composition of a contaminant material, as determined by the composition analyzer, may be used to formulate a recognition criterion for that contaminant material. A recognition criterion can be a characteristic or a combination of characteristics of a contaminant material which allows the contaminant material to be identified. In one example, the recognition criterion may include a contaminant ingredient concentration range for at least one contaminant ingredient within the contaminant material. The recognition criterion of each contaminant material may be stored in a non-transient memory.

In some cases, a carbon factor for each contaminant material in the feed of aluminum alloy wheels, indicative of a proportion of carbon in that contaminant may also be determined. The carbon factor of a contaminant may be based for example, on at least one contaminant ingredient within the contaminant material and may be indicative of the quantity of greenhouse gases that may be produced if the contaminant material is melted. The carbon factor may be stored in a non-transient memory and may be tied to a recognition criterion such that when a sample material is determined to correspond to a particular contaminant material, based on the recognition criterion, the carbon factor associated with that contaminant material may be applied to the sample material. Alternatively, a recognition criterion may have an associated carbon factor tied thereto so that when a recognition criterion is matched to a contaminant, the corresponding carbon factor may be applied to that contaminant.

Referring back to FIG. 1, in the example illustrated, the provided feed of aluminum alloy wheels may be fragmented into a plurality of fragments at step 104. The wheels may be fragmented by running the wheels through a fragmenting unit, such as an industrial shedder. Any suitable shredder known in the art may be used. For example, waste metal pieces may be supplied to a hopper of a conventional shredding apparatus, such as the SSI Series 45H shredder available from SSI Shredding Systems Inc. at 9760 SW Freeman Drive, Wilsonville, Oreg., 97070-9286, USA. This shredding apparatus may include a cutter box housing cutters, which can be mounted on parallel shafts that rotate horizontally in opposite directions. The feed hopper can be located above the cutter box. Due to the force of gravity, the waste metal pieces placed in the feed hopper can then be fed downwardly into the proper location where they can be engaged by the cutters and torn or cut into shreds.

The size of the fragments produced during the fragmenting process 104 may vary depending on the design and configuration of the fragmenting unit, for example, the size, spacing and orientation of shredders or cutters though fragments produced by the fragmenting process may be of substantially uniform size.

After being fragmented, at step 106, each fragment of the plurality of fragments may be shot blasted to at least partly remove at least one contaminant material present thereon. It is to be understood that not all fragments produced in step 104 may have at least one contaminant material present thereon. However, even if a fragment does not have at least one contaminant material present thereon, it may still be shot blasted as if it did.

During shot blasting, abrasive particles, i.e., a plurality of shot, can be projected at the fragments at high speed. The shot impacting the surfaces of the fragments can dislodge the contaminant materials deposited on the surfaces of the fragments, resulting in fragments with surfaces largely free from contamination. However, a first round of shot blasting may not remove all contaminant materials deposited on the surfaces of the fragments.

Shot blasting may be conducted in any suitable shot blasting apparatus. For example, the apparatus may be a centrifugal blasting apparatus, such as the model (FB-4/28/E/MR) Flexbel system available from BCP Wheelabrator of 1219 Corporate Drive, Burlington, Ontario, L7L 5V5, Canada, which is suitable for blast cleaning small parts. Abrasives may include steel shot, alumina, silica, and other abrasive materials.

The plurality of shot blasted fragments may be separated from the plurality of shot (depending on the form of cleaning that is used, other similar separation steps may be conducted). It may be desirable to separate the plurality of fragments from the plurality of shot because including the shot in the aggregate batch might negatively affect the material properties of the recycled material (i.e., might skew the aggregate batch composition away from a desired batch composition). Although desirable, in some examples, it may be impractical to completely separate the plurality of fragments from the plurality of shot. That is, in some examples, a portion of the plurality of fragments and the plurality of shot might be separated from the remaining plurality of fragments. Further, in some examples, a portion of the plurality of shot may not be separated from the remaining plurality of fragments.

After shot blasting, a representative sample of fragments of the plurality of fragments may be selected. As described in more detail below, the representative sample of fragments may be used to determine whether the batch of fragments from which the representative sample of fragments is selected contains too high a level of contaminants and should be (a) removed from the recycling process; or (b) returned for additional shot blasting.

Although desirable, it may be impractical to determine a contaminant material concentration estimate of each contaminant element for each fragment of the plurality of fragments (i.e., impractical to test each fragment of the plurality of fragments to determine if the plurality of fragments contains too high a level of contaminants or not). It may be impractical to test each fragment of the plurality of fragments due to the amount of time required to make a contaminant material concentration estimate. Accordingly, as illustrated in FIG. 1, in some examples, a subset of the plurality of fragments may be used as a representative sample of fragments of the plurality of fragments, and contaminant material concentration estimates for each contaminant material may be determined for only the fragments of the representative sample of fragments.

The representative sample of fragments should be sufficiently large to adequately represent the plurality of fragments. Any statistical method known in the art may be used to determine the minimum size of a smaller sample population required to statistically represent the larger population such that attributes of the larger population can be inferred from the attributes measured for the smaller population. In some examples, the subset of the plurality of fragments may be compared to the determined contamination level prior to fragmentation to determine the representativeness of the subset. In other examples, the subset of the plurality of fragments may be compared with known information about the distribution of contaminants within the feed of aluminum alloy wheels and/or individual aluminum wheels.

With the represented sample of fragments selected, each fragment of the representative sample of fragments may be inspected to identify any contaminant materials that may still be deposited thereon.

To identify the contaminant materials deposited on surfaces of the fragments of the representative sample of fragments, a recognition criterion stored in a computer readable non-transitory memory may be used.

As described above, the recognition criterion may include a contaminant ingredient concentration range for at least one contaminant ingredient of the contaminant material. Accordingly, using any composition analyzer known in the art, the composition of each fragment in the representative sample of fragments (including the contaminant) may be determined. In some examples, the composition analyzer may use radiation emitters to induce characteristic radiation to be emitted from the fragments. Other suitable composition analyzers may compare expected properties of a fragment with actual properties of the fragment. Using the recognition criterion, the composition measured by the composition analyzer may be matched to a specific contaminant or set of contaminants.

In some examples, each contaminant material may contain at least one contaminant ingredient and the recognition criterion for that contaminant material can include the contaminant ingredient concentration range for that ingredient. In some cases, the contaminant material may contain several ingredients and the recognition criterion may include the ingredient concentration range of each of the ingredients in the contaminant material. In some examples, the recognition criterion comprises a plurality of contaminant ingredients indicative of a contaminant material. That is, in some examples the contaminant may be identifiable by only determining a plurality of ingredients (i.e., the concentration of each ingredient in the contaminant material may not be needed to identify the contaminant material and the contaminant material may be identified based on a listing of ingredients measured by the composition analyzer).

The aluminum alloy wheels may be contaminated by a variety of contaminants and not all contaminants may contain only carbon. Accordingly, in some cases, the recognition criterion for a particular contaminant material can include a contaminant ingredient concentration range for a contaminant ingredient different from carbon, for example, a metal. In some other cases, while the contaminant material may contain carbon, the recognition criterion for a particular contaminant material may include a contaminant ingredient concentration range for a contaminant ingredient that does not contain carbon.

Some carbon-containing materials, such as some types of paints may include metals. In such cases, the at least one contaminant ingredient of the contaminant material can include a kind of metal, such as zinc or titanium, and the recognition criterion for the metal-containing material can include the contaminant ingredient concentration range for that kind of metal in the metal-containing material.

In cases where the at least one contaminant material includes more than one ingredient, for example two ingredients i.e., a first ingredient and a second ingredient, one of the two ingredients may be more easily detectable. For example, in metal-containing contaminant materials, metal may be more easily detectable than carbon and accordingly, the recognition criterion for that contaminant material may include the contaminant ingredient concentration range of the metal. For example, laser-induced breakdown spectroscopy (LIBS) may be used to detect the spectral signature of metal contained in the paint.

In some cases, identifying the types of contaminants in the aluminum wheels may also impact the type of shot blasting process that should be used, as some contaminants may be easier or more difficult to remove depending on the shot blasting process used.

With the represented sample of fragments selected, a carbon factor for each contaminant material of the at least one contaminant material may also be identified. The carbon factor may be indicative of the quantity of greenhouse gases that may be produced if the contaminant material is melted. In other words, a high carbon factor indicates a high concentration of carbon in the contaminant material and can indicate a corresponding high expected calculated carbon emission value.

Identifying the carbon factor may be based on at least one of the identified contaminant materials and the recognition criterion. That is, a recognition criterion may have an associated carbon factor tied thereto so that when a recognition criterion is matched to a contaminant the corresponding carbon factor may be applied to that contaminant. Alternatively, a contaminant may have an associated carbon factor, and once the contaminant is identified using the recognition criterion, the corresponding carbon factor may be identified for that contaminant based on the identification of the contaminant.

Like the recognition criterion, the carbon factor may be stored in a computer readable non-transient memory.

Each of the recognition criterion and the carbon factor may be determined by testing outside of the recycling process and may be stored in the computer non-transient memory prior to providing the feed of aluminum alloy wheels. Alternatively, the recognition criterion and in some cases, the carbon factor may be determined when the feed of aluminum alloy wheels is initially provided, prior to fragmentation.

Referring to the example illustrated in FIG. 1, with the represented sample of fragments selected, at step 110, a contaminant material concentration estimate may be determined for each contaminant material of each fragment in the representative sample of fragments of the plurality of fragments. In other examples, a contaminant material concentration estimate may be determined for each contaminant material for each fragment of the plurality of fragments.

A contaminant material concentration estimate is an estimate of the amount (by weight) of a contaminant material with respect to the weight of the fragment containing that contaminant material (for example on a surface of that fragment and/or affixed to that fragment). It is to be understood that materials not commonly found within the base alloy are not necessarily considered contaminant materials that are likely to be removed by further shot blasting or that are likely to increase greenhouse gas emissions. For example, fixtures attached to the alloy wheels that may need to be removed may not be considered contaminant materials. Methods for calculating a contaminant material concentration estimate are described in detail below (see, Determining the Contaminant Material Concentration Estimate).

It is also to be understood that as the aluminum alloy wheels may not be contaminated uniformly, the at least one contaminant material may not be uniformly distributed among the plurality of fragments. Accordingly, for each contaminant material, each fragment of the representative sample of fragments may have a unique contaminant material concentration estimate. Similarly, when the plurality of fragments contains two or more contaminant materials, the two or more contaminants may not be distributed evenly among the plurality of fragments and accordingly, a fragment in the representative sample of fragments may have a high contaminant material concentration of a first contaminant material and a low contaminant material concentration of a second contaminant material or vice versa. Because of the possible variation of contaminants amongst fragments, an accurate representative sample of fragments is required.

In some cases, when the at least one contaminant material includes a metal-containing material, the contaminant material concentration estimate may be determined by determining the contaminant material concentration estimate of the metal-containing contaminant material.

When the at least one contaminant material includes a metal-containing material, the metal-containing material ingredient may be more easily detectable than other ingredients contained in the metal-containing material and accordingly, the contaminant material concentration estimate for the metal-containing contaminant material may be more easily determined by detecting the metal than by detecting other ingredients. Determining the contaminant material concentration estimate may involve heating a surface of the fragment to a point where the surface emits a characteristic radiation while cooling down, operating a sensor to detect that characteristic radiation, and operating a processor to analyze the characteristic radiation to determine the composition measurements of the kind of metal contained within the material. This characteristic radiation, called "a spectral signature", may be compared with the spectral signature of aluminum alloy, to remove the effects of the spectral signature of the base aluminum alloy. In some cases, laser-induced breakdown spectroscopy (LIBS) may be used to detect the spectral signature of the contaminant material.

Since a single fragment may include multiple contaminant materials, in some examples a contaminant material concentration estimate may be determined for several contaminant elements of that fragment. For example, a fragment may contain two contaminant materials, i.e., a first contaminant material and a second contaminant material. Accordingly, at step 110, a first contaminant material concentration estimate of the first contaminant material may be determined and a second contaminant material concentration estimate of the second contaminant material may be determined.

After the contaminant material concentration estimate(s) are determined, at step 110, the plurality of fragments can be either approved or rejected by a data processor. The data processor can approve or reject the plurality of fragments based on an aggregate carbon emission calculation. The aggregate carbon emission calculation for each contaminant material can be based on the contaminant material concentration estimate determined at step 110 and the carbon factor of each contaminant material.

As the carbon level of each contaminant material in a fragment may contribute to the production of greenhouse gases when the fragment and all of its contaminant materials are melted, the aggregate carbon emission calculation may be based on an aggregate or a sum of the carbon contribution of each contaminant material for each fragment of the plurality of fragments. This calculation can be made by estimating contaminant material concentrations for each contaminant material and for each fragment. These estimates of contaminant material concentrations can be determined, for example, by determining, for each contaminant material, the aggregate contaminant material concentration for that contaminant material for the representative sample of fragments. Assuming the representative sample of fragments is truly representative of the plurality of fragments, the aggregate contaminant material concentration for each contaminant material for the representative sample of fragments, can then be attributed to the plurality of fragments (that is, we can assume that the plurality of fragments has approximately the same aggregate contaminant material concentrations for each contaminant material as the representative sample of fragments). An estimate of the carbon contribution of each contaminant material can be calculated based on the carbon factor of the contaminant material and the contaminant material concentration estimate for that contaminant material. That is, the estimate of the carbon contribution of each contaminant material in the plurality of fragments may be estimated from the carbon factor of the contaminant material and the contaminant material concentration estimate for that contaminant material as well as the total mass of the plurality of fragments.

Alternatively, for each contaminant material in the plurality of fragments, an average contaminant material concentration estimate may be determined, based on the contaminant material concentration estimate of each contaminant material of each fragment in the representative sample of fragments. Assuming the representative sample of fragments is truly representative of the plurality of fragments, the average contaminant material concentration estimate obtained for each contaminant material can be representative of the contaminant material concentration estimates of a notional fragment of the plurality of fragments. The aggregate carbon emission for the plurality of fragments can then be determined based on the contaminant material concentration estimates of this notional fragment, the carbon factor associated with each contaminant material, and the total mass of the plurality of fragments.

Alternatively, an aggregate carbon emission of each fragment in the representative sample of fragments may be determined, based on, for each fragment in the representative sample of fragments, the contaminant material concentration estimate of each contaminant material and the carbon factor associated with each of the contaminant materials. The aggregate carbon emission of the representative sample of fragments may be determined by summing the aggregate carbon emission of each fragment in the representative sample of fragments. The aggregate carbon emission calculation of the plurality of fragments may be estimated from the aggregate carbon emission of the representative sample of fragments and the mass of the representative sample of fragments relative to the mass of plurality of fragments. In some cases, the aggregate carbon emission calculation for the plurality of fragments may also determined by estimating the individual carbon emission of each fragment of the plurality of fragments, and summing the individual carbon emissions of each fragment.

In cases where the plurality of fragments include at least two contaminants comprising at least a first contaminant material and a second contaminant material, the aggregate carbon emission calculation can involve determining a first contaminant material carbon contribution based on the first contaminant material concentration estimate and the carbon factor for the first contaminant material and determining a second contaminant material carbon contribution based on the second contaminant material concentration estimate and the carbon factor for the second contaminant material. In such cases, the aggregate carbon emission calculation can be based at least in part on a sum of the first and second material carbon contributions. In some cases, the carbon factor for each of the first and second contaminant material may be retrieved from the non-transient memory. The carbon factors for different materials may be different, as some materials may comprise a much higher proportion carbon than others. That is, the carbon factor of the first contaminant material may differ from the carbon factor of the second contaminant material, such that the expected contributions of both the first and second contaminant materials can be calculated using their respective and different carbon factors. For example, if the plurality of fragments include rubber and paint contaminants, the rubber carbon contribution and the paint carbon contribution may be summed as part of the aggregate carbon emission calculation.

If the representative sample of fragments is found to only contain one contaminant material, the aggregate carbon emission calculation can be based only on the aggregate carbon emission calculations for that contaminant material.

If the representative sample of fragments is found to contain, for example, three contaminant materials, the aggregate carbon emission calculation can be based on the carbon contribution of each of the three contaminant materials, the carbon contribution of each contaminant being based on the contaminant material concentration estimate of the contaminant material for the representative sample of fragments and the carbon factor for that contaminant material. That is, the aggregate carbon emission calculation for the plurality of fragments can be based on each of the aggregate contaminant material concentration estimates of each contaminant of the representative sample of fragments of the plurality of fragments.

The aggregate carbon emission calculation may be used by the data processor to either approve or reject the plurality of fragments. For example, the aggregate carbon emission calculation may be compared with a predetermined threshold. The threshold may correspond to a maximum allowable or tolerable quantity of carbon emissions. This maximum allowable or tolerable quantity of carbon emissions may vary directly with the mass of the plurality of fragments being recycled (that is, the larger the mass of the plurality of fragments being recycled, the larger the maximum allowable or tolerable quantity of carbon emissions). If the aggregate carbon emission calculation is below the threshold, the data processor may approve the plurality of fragments and the plurality of fragments may be provided to a downstream recycling process to produce a target aluminum alloy. If the aggregate carbon emission calculation is above the threshold, the data processor may reject the plurality of fragments and the plurality of fragments may be further shot blasted, further cleaned in some other manner, or discarded. In some cases, a high aggregate carbon emission calculate may indicate an upstream problem, such as inadequate shot blasting of the fragments, or that some alloy wheels were too contaminated to be recycled.

When the plurality of fragments is approved, the plurality of fragments may be provided to a downstream recycling process to produce a target aluminum alloy.

When the plurality of fragments is rejected, the plurality of fragments may be discarded or returned to step 106 for further shot blasting to further remove contaminants from the plurality of fragments. That is, expected carbon emissions that may be produced by heating the fragments may be above an acceptable threshold for carbon emissions. Accordingly, the fragments may need to be further shot blasted to reduce the carbon emission calculation of the fragment to an acceptable level.

A system for recycling aluminum alloy wheels may comprise series transfer mechanisms in addition to the equipment discussed above, e.g., fragmenting unit, cleaning unit, and composition analyzer. For example, a transfer mechanism may be used to provide the representative sample of fragments to the composition analyzer, for example a laser spectroscopy analyzer. The transfer mechanisms may include one or more of, or a combination of one or more of: a conveyor, a pick-and-place unit, a robotic arm, and other relevant technologies known in the art, selected based on the geometry and size of the rims and/or fragments to be moved. Similar transfer mechanisms may be employed to transport the rims and/or fragments from the composition analyzer to other stations in the recycling process, and between the other stations that may be part of the recycling process.

The data processor may include a computer comprising a non-transient memory and a processor in electronic communication with the non-transient memory. The non-transient memory may have stored thereon an aggregate carbon emission threshold, a recognition criterion for each contaminant material and a carbon factor for each contaminant material. The computer may be in electronic communication with the composition analyzer to receive, for each fragment in the representative sample of fragments of the plurality of fragments, the contaminant material estimate and the carbon factor of each contaminant material on that fragment, and the processor may be operable to determine the aggregate carbon emission calculation and approve or reject the plurality of fragments based thereon.

In some cases, the methods described herein may be used in combination with materials handling or air injection technology to remove some fragments from the stream. For example, based on the assessed distribution of contaminants, when the aluminum alloy wheels are fragmented, highly contaminated fragments that may not be shot blasted efficiently may be removed from the stream and fragments that are unlikely to be contaminated may be removed from the stream and provided downstream to the recycling process.

Determining the Contaminant Material Concentration Estimate

Any method known in the art to measure the concentration of a contaminant with respect to a fragment to which that contaminant is affixed to and/or on a surface of, may be used. In some examples, a laser scanner can be used to measure the concentration of contaminants in a representative sample of fragments. This can involve using a laser to heat the material at a point on the surface of a representative fragment to a temperature at which that material will emit a characteristic radiation while cooling down. A sensor can then be operated to detect that characteristic radiation to provide a spectrum of signal magnitudes at different frequencies. This spectrum of signal magnitudes at different frequencies can then be analyzed by a computer processor to infer the relative concentrations of different elements within the alloy, as described, for example, in U.S. Pat. No. 10,220,418, incorporated herein by reference. If the type of base alloy is known (i.e., which elements are expected to be detected by the sensor), the computer processor can infer which elements are "contaminant elements" and which are "alloy elements". Accordingly, the concentration of contaminant elements can be determined.

A single concentration measurement may be made on each fragment of the representative sample of fragments. The location of this measurement may affect the contaminant material concentration estimate. For example, if a measurement is made directly on a rust spot, the contaminant material concentration estimate will be different than if the measurement, on the same fragment, was made adjacent to the rust spot. Accordingly, in some examples, multiple concentration measurements may be made of each fragment of the representative sample of fragments. That said, the concentration measurements are to be understood as estimates. It is to be understood that if enough measurements are made on enough fragments, based on statistical analysis, an accurate estimate of the contaminant material concentrations can be made.

In one example, a "Laser-Induced Breakdown Spectroscopy" ("LIBS") composition analyzer manufactured by Laser Distance Spectrometry can be adapted as the laser scanner and sensor. The LIBS composition analyzer may include a radiation emitter, such as an Nd:YAG laser. The laser may shine at a frequency ranging from 1 to 20 hertz, thereby raising the temperature of the fragments at the point of contact between the fragment and the laser to above 30,000 degrees Celsius and generating plasma. The plasma may quickly cool down, returning the energized ions to a low energy state. While returning to the low energy state, the ions may emit characteristic radiation. The LIBS composition analyzer may contain one or more sensors that detect the characteristic radiation. A processor may then analyze readings obtained from the sensors and determine from them the concentration of the constituents contained in the material undergoing the temperature change. The processor may be disposed within the composition analyzer. Alternatively, the processor may be a remote processor.

Other suitable composition analyzers may include composition analyzers that use laser spectroscopy or other systems that rely on other methods of inducing characteristic radiation to be emitted by a material of each fragment at a surface of that fragment and detecting and analyzing that characteristic radiation to determine a composition of that material. The composition analyzers may detect the characteristic radiation by using any suitable sensor—for example, suitable sensors may include complementary metal-oxide-semiconductor (CMOS), high density, short channel metal-oxide-semiconductor (HMOS), charge-coupled device (CCD), and other types of sensors.

Suitable composition analyzers may use, for example, radiation emitters such as plasma, electron beam, or any other radiation emitters suitable to heat a material of each fragment in at least one spot on a surface of that fragment to a point where the material will emit a sufficient quantity and quality of characteristic radiation while cooling down so as to permit a sensor to detect that characteristic radiation and to allow for a processor to determine a composition of the material from that characteristic radiation. The composition analyzer can be adapted to withstand continuous use, as well as typical conditions that may be present in a particular waste metal recycling operation. Such conditions may include vibrations resulting from the operation of transfer mechanisms, and dust and other particles produced in the recycling process.

Alternatively, other means of detecting composition not involving measuring characteristic radiation may be used.

The present invention has been described here by way of example only. Various modification and variations may be made to these exemplary embodiments without departing from the spirit and scope of the invention, which is limited only by the appended claims.

I claim:

1. A method of recycling aluminum alloy wheels, the method comprising:
   providing a feed of aluminum alloy wheels of a particular alloy;
   fragmenting the aluminum alloy wheels into a plurality of fragments;
   shot blasting the plurality of fragments to at least partly remove at least one contaminant material, each contaminant material of the at least one contaminant material i) comprising at least one of paint, plastic or rubber, ii) containing carbon, and iii) being combustible;
   storing in a computer readable non-transient memory, at least one recognition criterion and at least one carbon factor, wherein
      for each contaminant material of the at least one contaminant material, the at least one recognition criterion comprises a recognition criterion for that contaminant material, and
      for each contaminant material of the at least one contaminant material, the at least one carbon factor comprises a carbon factor for that contaminant material, the carbon factor indicating a proportion of carbon in that contaminant material such that combustion of a quantity of that contaminant material would produce a corresponding quantity of carbon emissions calculable using the carbon factor;

for each fragment of a representative sample of fragments of the plurality of fragments, for each contaminant material of the at least one contaminant material, using the recognition criterion for that contaminant material to determine a contaminant material concentration estimate for that fragment;

operating a data processor to either approve or reject the plurality of fragments, based on an aggregate carbon emission calculation for the plurality of fragments, the aggregate carbon emission calculation being based on, for each contaminant material of the at least one contaminant material, and for each fragment of the representative sample of fragments, the contaminant material concentration estimate and the carbon factor for that contaminant material;

when the plurality of fragments is approved, providing the plurality of fragments to a downstream recycling process to produce a target aluminum alloy; and when the plurality of fragments is rejected, further shot blasting the plurality of fragments to further remove the at least one contaminant material.

2. The method as defined in claim 1 wherein the at least one contaminant material is at least two contaminant materials, comprising at least a first contaminant material and a second contaminant material;

for each fragment of the representative sample of fragments, determining, for each contaminant material of the at least two contaminant materials, the contaminant material concentration estimate for that fragment, comprises determining a first contaminant material concentration estimate for the first contaminant material in that fragment and a second contaminant material concentration estimate for the second contaminant material in that fragment; and, operating the data processor to either approve or reject the plurality of fragments based on the aggregate carbon emission calculation for the plurality of fragments, comprises determining a first contaminant material carbon contribution based on the first contaminant material concentration estimate and the carbon factor for the first contaminant material, determining a second contaminant material carbon contribution based on the second contaminant material concentration estimate and the carbon factor for the second contaminant material, and making the aggregate carbon emission calculation based at least partly on a sum of the first contaminant material carbon contribution and the second contaminant material carbon contribution.

3. The method as defined in claim 1 wherein the carbon factor for the first contaminant material differs from the carbon factor for the second contaminant material.

4. The method as defined in claim 1 wherein the recognition criterion comprises a contaminant ingredient concentration range for at least one contaminant ingredient of that contaminant material.

5. The method as defined in claim 4 wherein a contaminant ingredient of the at least one contaminant ingredient is different from carbon.

6. The method as defined in claim 4 wherein a contaminant ingredient of the at least one contaminant ingredient does not contain carbon.

7. The method as defined in claim 4 wherein the at least one contaminant material comprises a metal-containing material, the at least one contaminant ingredient for that metal-containing material comprises a kind of metal; and the recognition criterion for that metal-containing material comprises the contaminant ingredient concentration range for that kind of metal in the metal-containing material.

8. The method as defined in claim 7 wherein the kind of metal is zinc or titanium.

9. The method as defined in claim 7 wherein the metal-containing material comprises paint.

10. The method as defined in claim 7 wherein, for each fragment of the representative sample of fragments of the plurality of fragments, determining, for the metal-containing material, a contaminant material concentration estimate for that fragment comprises heating a surface of the fragment to a point where the surface will emit a characteristic radiation while cooling down, operating a sensor to detect that characteristic radiation, and operating a processor to analyze the characteristic radiation to determine the composition measurements of the kind of metal contained within that material.

11. The method as defined in claim 1 wherein the recognition criterion comprises a plurality of contaminant ingredients indicative of that contaminant material.

12. A method of recycling aluminum alloy wheels, the method comprising:

providing a feed of aluminum alloy wheels of a particular alloy;

fragmenting the aluminum alloy wheels into a plurality of fragments;

shot blasting the plurality of fragments to at least partly remove at least one contaminant material, each contaminant material of the at least one contaminant material i) comprising at least one of paint, plastic or rubber, ii) containing carbon, and iii) being combustible;

after shot blasting, selecting a representative sample of fragments from the plurality of fragments;

for each fragment of the representative sample of fragments of the plurality of fragments, for each contaminant material of the at least one contaminant material, using a recognition criterion for that contaminant material to determine a contaminant material concentration estimate for that fragment, wherein the recognition criterion for that contaminant material is stored in a computer readable non-transitory memory, operating a data processor to either approve or reject the plurality of fragments, based on an aggregate carbon emission calculation for the plurality of fragments, the aggregate carbon emission calculation being based on, for the at least one non-removed contaminant material of the at least one contaminant material, and for each fragment of the representative sample of fragments, the contaminant material concentration estimate and a carbon factor for that non-removed contaminant material, wherein the carbon factor for that non-removed contaminant material is stored in the computer readable non-transitory memory.

13. The method as defined in claim 12, further comprising, prior to the operating step, storing at least one of the recognition criterion and the carbon factor in the computer readable non-transient memory.

14. The method as defined in claim 12, further comprising providing the plurality of fragments to a downstream recycling process to produce a target aluminum alloy when the plurality of fragments is approved.

15. The method as defined in claim 14, further comprising providing the plurality of fragments to a shot blaster for further shot blasting when the plurality of fragments is rejected.

16. The method as defined in claim 14, further comprising discarding the plurality of fragments when the plurality of fragments is rejected.

17. The method as defined in claim 12, further comprising providing the plurality of fragments to a shot blaster for further shot blasting when the plurality of fragments is rejected.

18. The method as defined in claim 12, further comprising discarding the plurality of fragments when the plurality of fragments is rejected.

\* \* \* \* \*